(12) United States Patent
Cannestra

(10) Patent No.: US 11,745,248 B2
(45) Date of Patent: Sep. 5, 2023

(54) NEEDLE BENDER

(71) Applicant: Blue Fury Consulting, LLC, Jacksonville, FL (US)

(72) Inventor: Andrew F. Cannestra, Jacksonville, FL (US)

( * ) Notice: Subject to any disclaimer, the term of this patent is extended or adjusted under 35 U.S.C. 154(b) by 0 days.

(21) Appl. No.: 17/918,934

(22) PCT Filed: May 13, 2021

(86) PCT No.: PCT/US2021/032159
§ 371 (c)(1),
(2) Date: Oct. 14, 2022

(87) PCT Pub. No.: WO2021/231682
PCT Pub. Date: Nov. 18, 2021

(65) Prior Publication Data
US 2023/0124504 A1    Apr. 20, 2023

Related U.S. Application Data

(60) Provisional application No. 63/024,818, filed on May 14, 2020.

(51) Int. Cl.
*B21G 1/08* (2006.01)
*B21F 1/00* (2006.01)
*A61B 17/06* (2006.01)

(52) U.S. Cl.
CPC ............... *B21G 1/08* (2013.01); *B21F 1/002* (2013.01); *A61B 17/06066* (2013.01)

(58) Field of Classification Search
CPC .......... B21D 7/021; B21D 7/024; B21D 7/04; B21D 9/055; B21F 1/002; B21G 1/08; A61B 17/06066
See application file for complete search history.

(56) References Cited

U.S. PATENT DOCUMENTS 2,864,272 A * 12/1958 Swanson ............ B21F 1/06
                                                72/309
3,172,452 A *  3/1965 Bryant .............. B21D 7/024
                                                72/477

(Continued)

FOREIGN PATENT DOCUMENTS

CN      110893446          3/2020
DE         596692 C  *  5/1934 ............ B21D 7/021

(Continued)

OTHER PUBLICATIONS

DE 19718937 A1, Gunthner Nov. 1998.*

(Continued)

*Primary Examiner* — Edward T Tolan
(74) *Attorney, Agent, or Firm* — WARNER NORCROSS + JUDD LLP

(57) ABSTRACT

A needle bender for custom bending of needles to different desired needle bend radii is provided. The needle bender can include abase and a shaper coupled to the base through a support member. The shaper may have a plurality of grooves corresponding to different desired needle bend radii. A leverage arm with a needle slide disposed on one end may be rotatably coupled to the support arm. When a needle is inserted along the base into one of the grooves in the shaper and at least partially into the needle slide, the leverage arm can be actuated toward the base to thereby bend the needle to the desired needle bend radius. The needle bender may also include a lock plate between the base and the shaper that can be actuated toward the shaper to further secure the needle to the shaper.

18 Claims, 6 Drawing Sheets

(56) References Cited

U.S. PATENT DOCUMENTS

| | | | | |
|---|---|---|---|---|
| 4,522,055 | A | * | 6/1985 | Berger .................... B21D 7/02 |
| | | | | 81/487 |
| 4,926,672 | A | * | 5/1990 | Swanson ................ B21D 7/063 |
| | | | | 72/157 |
| 5,499,521 | A | * | 3/1996 | Luikart .................. B21D 7/024 |
| | | | | 72/157 |
| 5,526,666 | A | | 6/1996 | Bogart et al. |
| 2010/0263425 | A1 | | 10/2010 | Matsutani et al. |
| 2012/0197317 | A1 | * | 8/2012 | Lezama ................ A61F 2/4611 |
| | | | | 606/86 A |
| 2013/0172930 | A1 | | 7/2013 | Matsutani et al. |

FOREIGN PATENT DOCUMENTS

| | | | | | |
|---|---|---|---|---|---|
| GB | | 2051632 A | * | 1/1981 | ............. B21D 7/024 |
| GB | | 2206069 A | * | 12/1988 | ............. B21D 7/024 |
| KR | 20-0386173 | | | 6/2005 | |

OTHER PUBLICATIONS

Translation DE 19718937 A1, Gunthner Nov. 1998.*
KR2012048069 A, Kim May 2012.*
International Search Report and the Written Opinion of the International Searching Authority for International Application No. PCT/US2021/032159 dated Sep. 10, 2021.

* cited by examiner

NEEDLE BENDER

RELATED APPLICATIONS

The present application claims the benefit of U.S. Provisional Patent Application No. 63/024,818, filed May 14, 2020, which is incorporated herein by reference in its entirety.

BACKGROUND

The present invention relates to the bending of surgical suture needles and trocars, and more particularly to the custom bending of needles, trocars, and instruments to different radii intraoperatively.

Needles and trocars used in surgery are manufactured with a specific radius of curvatures or bends in order to perform perforation of tissue. Many different radii of needles may be required throughout a given procedure. During a procedure, a surgeon may need to change the radius of a given needle rather than switch to a different needle having the desired radius. It can be critical to obtain the right bend in order to pass the suture or material into a tight surgical space. The requirement to change the bend can occur when the needle has already been used and suture or tubing has already passed through tissue.

Historically, bending the needle has been done with non-specific surgical instruments and manual force. One example of such an instrument is a "French style" bender. Bending the needle in this way carries a risk of needle stick and, if the needle has already been used in the procedure, infection or contamination of the surgeon and staff. Additionally, the manual method may not allow the radius of the needle to be reliably adjusted thereby requiring multiple bends and increasing the chance of injury to the surgeon and the staff.

BRIEF SUMMARY

The present disclosure provides a needle bender. The needle bender can perform controlled bends in the operative field. In one embodiment, the needle bender may have a base including a base arm and a support member coupled to a shaper. The shaper may have a curved outer surface and a plurality of grooves in the curved outer surface. Each of the plurality of grooves may correspond to a different desired needle bend radius. A leverage arm can be rotatably coupled to the support member for rotation about an axis. The leverage arm may rotate relative to the shaper or the leverage arm and the shaper may rotate as one unit. The leverage arm may have a needle slide disposed at one end that is configured to support at least a portion of a needle to be bent. The needle can be slid along the base arm and into one of the grooves in the shaper such that a portion contacts the needle slide. The leverage arm may then be actuated toward the base thereby moving the needle slide to push the needle into the groove of the shaper and forming the needle to the desired needle bend radius.

In one embodiment, the needle bender may include a lock plate between the base arm and the shaper. The lock plate may be secured to the base through one or more set screws. The set screws can be turned to raise the lock plate toward the shaper and lower the lock plate away from the shaper. Once a needle is inserted along the base, the set screws can move the lock plate upward to further secure the needle to the shaper. After the needle has been bent to the desired needle bend radius, the set screws can move the lock plate downward to release the needle from the shaper and allow the newly bent needle to be removed from the needle bender.

These and other objects, advantages, and features of the invention will be more fully understood and appreciated by reference to the detailed description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components. Any reference to claim elements as "at least one of X, Y and Z" is meant to include any one of X, Y or Z individually, and any combination of X, Y and Z, for example, X, Y, Z; X, Y; X, Z; and Y, Z.

DETAILED DESCRIPTION

The term "needle" is used throughout the disclosure to refer to needles, trocars, and other surgical instruments and devices unless otherwise noted.

Figure 1:
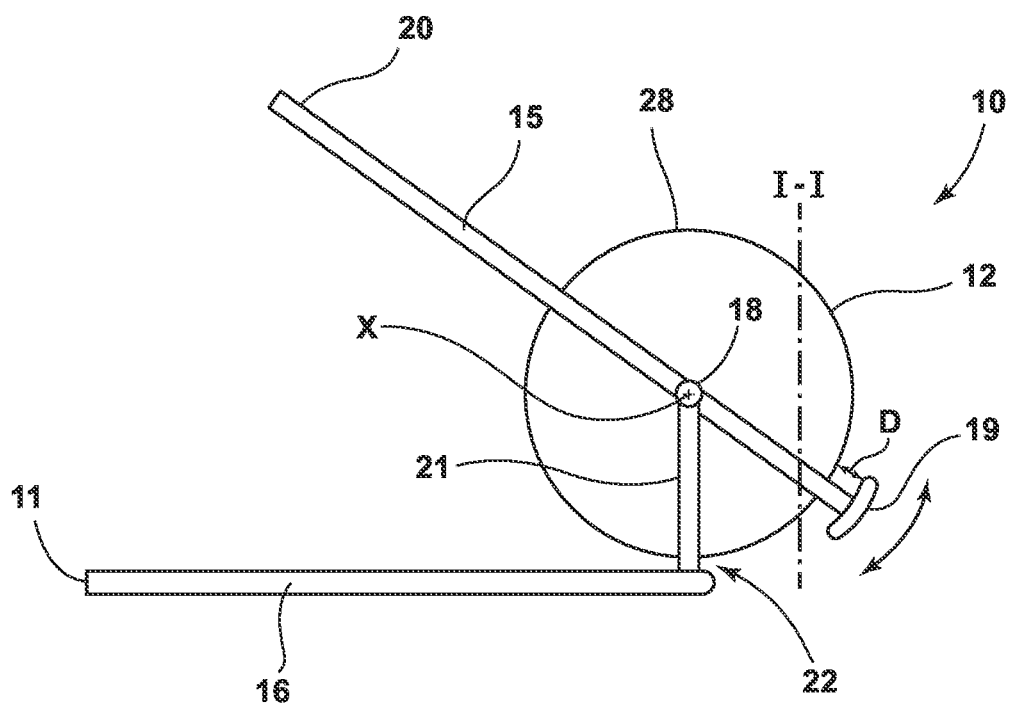
FIG. 1 depicts a side view of a needle bender according to one embodiment.
Figure 2:
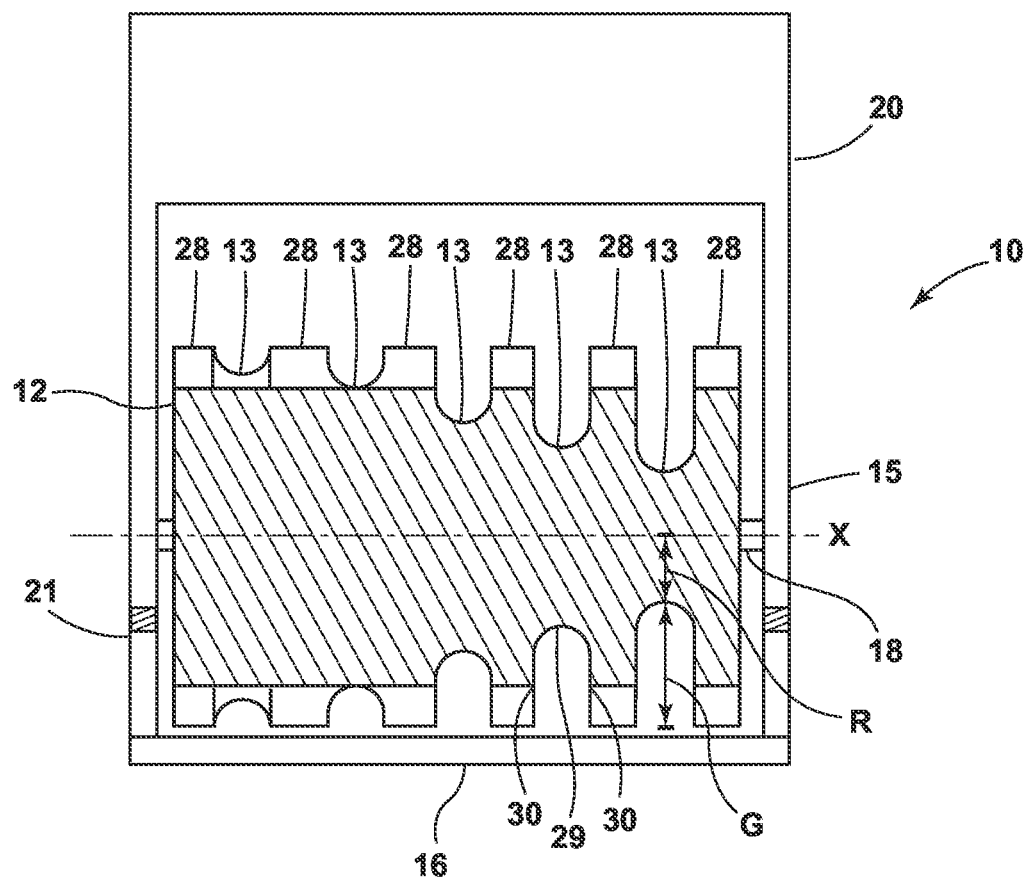
FIG. 2 depicts a front sectional view of the needle bender of FIG. 1 along the line I—I.

In FIGS. 1-2, a needle bender 10 according to one embodiment is shown. The needle bender 10 may include a base 11, and the base 11 may include a base arm 16 and a support member 21 coupled to the base arm 16. In one embodiment, the base arm 16 can be mounted to a stand or otherwise be fixed or stationary. A central shaft or axle 18 can be coupled to the support member 21 and may extend perpendicularly from the support member 21. In an alternative embodiment, the central axle 18 may extend from the support member 21 at any other suitable angle. The central axle 18 may define an axis X. As shown in FIG. 2, a second support member 21 can be coupled to the base arm 16 on the opposite end of the central axle 18, such that the central axle 18 is supported on either end by one of the support members 21. Additionally, or alternatively, the central axle 18 may be coupled to a stopper surface flared at the end opposite the support member 21, the stopper surface configured to retain a shaper 12 on the central axle 18 when the needle bender 10 includes only one support member 21.

A shaper 12, also referred to herein as a bending shaper, may be coupled to the central axle 18 and comprises a curved outer surface 28 disposed radially outwardly from and curving at least partially around the axis X of the axle 18. In a preferred embodiment, the shaper 12 may be coaxially disposed on the central axle 18. As descried in further detail below, the shaper 12 can minimize frictional forces between the needle bender 10 and a needle to be bent, and can minimize possible breakage or kinking of the needle.

The shaper 12 may be cylindrical, conical, or any other shape with a curved outer surface. The shaper 12 may define a single structure. Additionally, or alternatively, the shaper 12 can have a stepped shape comprising a series of round or cylindrical sections that define different radii of curvature bends to be applied to a needle to be bent.

In one embodiment, the shaper 12 can be fabricated as a single piece. In another embodiment, the shaper 12 may be fabricated as multiple pieces joined together through any suitable means. Suitable materials for the shaper 12—and the other components of the needle bender 10—will be known to those skilled in the art.

The shaper 12 can include a plurality of grooves 13 in the curved outer surface 28, each of the grooves 13 having a different diameter corresponding to a desired needle bend radius. This means that the needle bender 10 can be a single instrument that can provide a number of different smooth radii of curvature bends. The grooves 13 may be separated by portions of the curved outer surface 28. In one embodiment, the grooves 13 may be circumferential. While the grooves 13 may have varying shapes, in some embodiments, each groove 13 is defined by a groove base 29 and a pair of spaced walls 30 extending from the groove base 29 to the outer surface 28 of the shaper 12.

In one embodiment, the shaper 12 may be configured to rotate relative to the central axle 18, with the axle 18 being non-rotatable or fixed to the support member 21 and be stationary relative to the axis X. In an alternative embodiment, the shaper 12 can be stationary with respect to central axle 18, with the shaper 12 having a fixed radial orientation on the axle 18. In yet another embodiment, the shaper 12 can be directly coupled to the support member 21 and the axle 18 may be eliminated. In an alternative embodiment, the axle 18 may be rotatably mounted to the support member 21 and rotate relative to the axis X.

Regardless of how the shaper is mounted, the shaper 12 is spaced from the base arm 16. The space between the base arm 16 and the shaper 12, referred to herein as a needle gap 22, defines an opening with a height sufficient to fit needles of a variety of gauges between the base arm 16 and the shaper 12.

In the embodiment of FIG. 2, the shaper 12 is cylindrical with the plurality of grooves 13 of varying depths G resulting in different radii R. As used herein with respect to the shaper 12, the depth G of a groove 13 is the radial distance between the outer surface 28 and the groove base 29 of the groove 13, and the radius R of a groove 13 is the radial distance between the axis X and the groove base 29 of the groove 13. With reference to FIG. 2 and in a direction from left to right, each successive groove 13 is a deeper crevice in the shaper 12 such that each successive groove 13 has a smaller radius R. In an alternative embodiment, the varying depths of the grooves 13 can be arranged in any other suitable manner. The width of the grooves 13, defined between the space walls 30, may be configured to allow for a variety of needle gauges. As depicted, the shaper 12 has five grooves 13. In alternative embodiments, the shaper 12 may have any suitable number of grooves 13.

Referring again to FIG. 1, a leverage arm 15, also referred to herein as moveable leverage arm, may be movably coupled to the support member 21 through the central axle 18 and rotate about the axis X. In an alternative embodiment, the leverage arm 15 can rotate independently about another axis parallel to but spaced apart from the axis X. With a needle loaded into the needle gap 22, movement of the leverage arm 15 can apply a bending force to the needle.

In one embodiment, the shaper 12 and the leverage arm 15 rotate as one unit. In another embodiment, the leverage arm 15 and the shaper 12 can be independently rotatable about the central axle 18, with the shaper 12 free to rotate to minimize frictional forces between the needle bender 10 and a needle to be bent. In yet another embodiment, the leverage arm 15 rotates about the axis X while the shaper 12 remains stationary, e.g. does not rotate. Additionally, or alternatively, the leverage arm 15 can be mounted on hinges to a center of the shaper 12, or otherwise be pivotally or moveably mounted relative to the base arm 16. The leverage arm 15 and the base arm 16 can be approximately the same length, or have different lengths.

The leverage arm 15 may have a needle slide 19 disposed at one end such that the needle slide 19 is adjacent to and spaced from the curved outer surface 28 of the shaper 12 by a distance D. In one embodiment, the distance D may be equal to the height of the needle gap 22. In an alternative embodiment, the distance D may be greater than or less than the height of the needle gap 22. The needle slide 19 may have a hole therethrough or a needle channel 26 (see FIGS. 5A-5C) therein to receive a needle to be bent. As the leverage arm 15 moves toward the base arm 16, the needle slide 19 may guide the needle to be bent toward the groove 13 thereby bending the needle to the desired radius.

The leverage arm 15 may comprise a handle 20 disposed on an opposite end of the axis X from the needle slide 19. In one embodiment, the handle 20 may be made from medical grade silicone. With reference to the orientation of FIG. 1, lowering the handle 20 toward the base arm 16 pivots the leverage arm 15 counterclockwise about the axis X and raises the needle slide 19 upwardly. Raising the handle 20 away from the base arm 16 pivots the leverage arm 15 clockwise about the axis X and lowers the needle slide 19. Preferably, the handle 20 may lower the needle slide 19 at least until it is sufficiently aligned with the base arm 16 in a position ready to receive a needle.

In a preferred embodiment, the leverage arm 15 can be manually operated, with input force to the handle 20 being provided by a user. In another embodiment, the leverage arm 15 can be automated operated, with input force to the handle 20 being provided by an electrical or pneumatic actuator.

In one embodiment, a spring (not shown) can bias the handle 20 toward a raised or ready position where the needle slide 19 is adjacent to and aligned with the base arm 16, e.g. in a position ready to receive a needle. As an input force is applied to the handle 20, the spring may compress and allow the handle 20 to move toward the base arm 16. When the input force is removed, the spring may expand to return the handle 20 to its raised or ready position.

Figure 3:
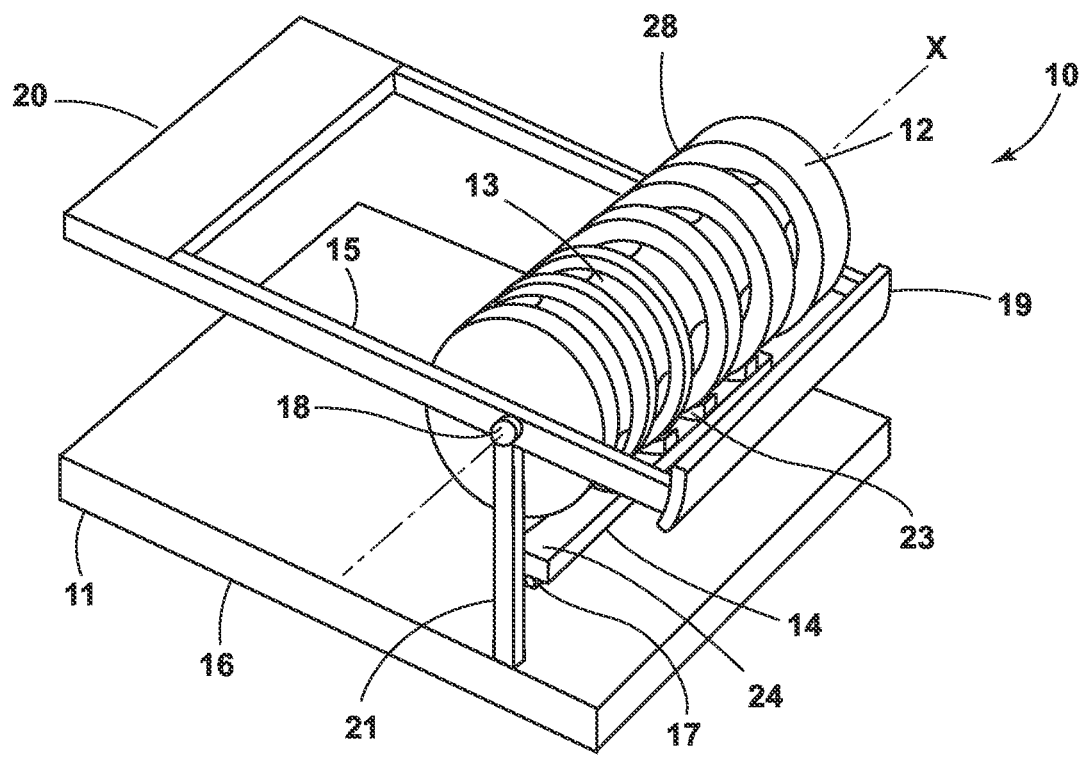
FIG. 3 depicts a perspective view of a needle bender according to another embodiment.

FIG. 3 depicts another embodiment of the needle bender 10. The needle bender 10 may further include a lock plate 14 for securing a needle at a desired location along the shaper 12. Put another way, the lock plate 14 can allow a needle to be anchored to the shaper 12, and can prevent lateral shifting of the needle during bending. The lock plate 14 may be located between the base arm 16 and the shaper 12, with the needle gap 22 defined between the lock plate 14 and the shaper 12. In one embodiment, the lock plate 14 can be mounted along the base arm 16 such that the lock plate 14 provides a point of leverage for bending a needle, with the needle gap 22 defined between an upper needle engaging surface 24 of the lock plate 14 and the shaper 12.

The lock plate 14 may be coupled to the base arm 16 through at least one set screw 17. The lock plate 14 may move toward the shaper 12 as the set screw 17 is turned in one direction, to secure a needle at a desired location along the shaper 12, such as within a particular one of the grooves 13. To release a needle, the lock plate 14 may move away from the shaper 12 as the set screw 17 is turned in the other direction. For example, the lock plate 14 may move toward the shaper 12 when the set screw 17 is turned clockwise and the lock plate 14 may move away from the shaper 12 when the set screw 17 is turned counterclockwise. Movement of the lock plate 14 relative to the shaper 12 also accommodates a variety of gauges (diameters) of needles.

The lock plate 14 may have the upper needle engaging surface 24 that confronts the outer surface 28 of the shaper 12 and defines the needle gap 22. The upper needle engaging surface 24 may be substantially planar or without feature, or may have features for gripping, holding, or locating a needle. In one embodiment, the upper needle engaging surface 24 includes a plurality of ridges 23 arranged offset from the grooves 13 of the shaper 12 corresponding to a desired radius of curvature such that the needle can be secured to the shaper 12 with the same force regardless of the depth G of the groove 13. Additionally, or alternatively, the ridges 23 and/or an upper needle engaging surface 24 may include a plurality of lock plate grooves aligned with the shaper grooves 13, wherein the lock plate grooves help align and guide a needle to be bent. The lock plate grooves may have a suitable width to accommodate a variety of needle gauges.

Figure 4:
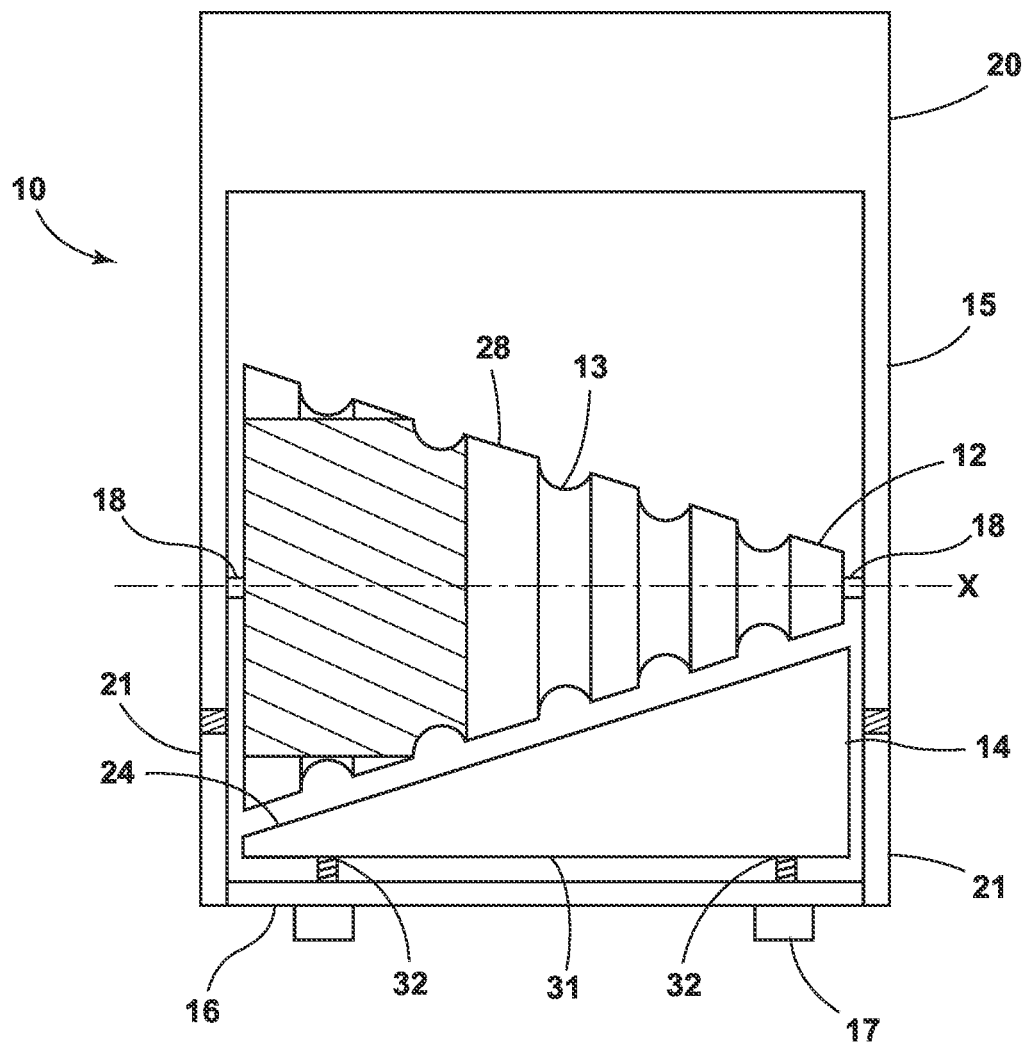
FIG. 4 depicts a front sectional view of a needle bender offset from an axis X according to yet another embodiment.

In FIG. 4, an alternative embodiment of the needle bender 10 with a front sectional view taken offset from axis X, in a location corresponding to line I—I shown for the embodiment of FIG. 1. As depicted, the shaper 12 is conical with a plurality of grooves 13 separated by portions of the curved outer surface 28. The needle bender 10 may include the lock plate 14. The lock plate 14 can have the upper needle engaging surface 24 and a base arm engaging surface 31. The base arm engaging surface 31 may define at least one opening 32 to movably couple the at least one set screw 17 to the lock plate 14. As depicted, the upper needle engaging surface 24 is diagonal on substantially the same angle as the shaper 12 and is angled relative to the base 11. This may allow the upper needle engaging surface 24 to engage a needle to be bent when placed in any of the grooves 13 with the same amount of force. Additionally, or alternatively, the upper needle engaging surface 24 may include a plurality of lock plate grooves aligned with the shaper grooves 13 wherein the lock plate grooves may help guide a needle to be bent along the lock plate 14. It is noted that while the embodiment shown in FIG. 4 includes a pair of set screws 17, it is understood that any number of set screws 17 could be used, including one set screw 17, or three or more set screws 17. While the embodiment shown herein uses set screws 17 to adjust and fix the lock plate 14 relative to the shaper 12, other adjustment mechanisms are possible. For example, a clamp or other fastening device can be used to hold the lock plate 14 and shaper 12 together.

Figure 5A:
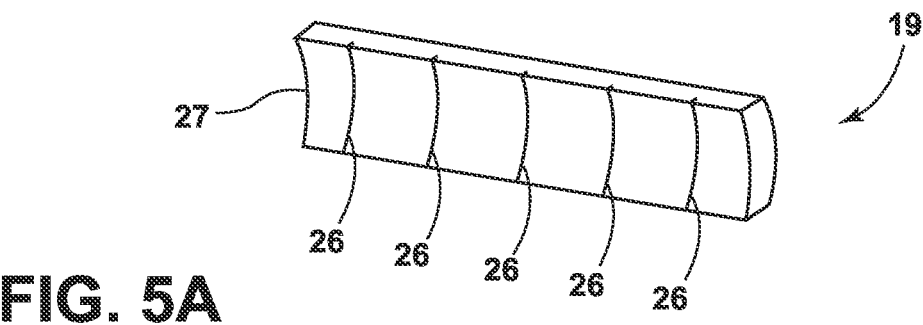
FIG. 5A depicts a perspective view of a needle slide for use with a cylindrical shaper according to one embodiment.
Figure 5B:
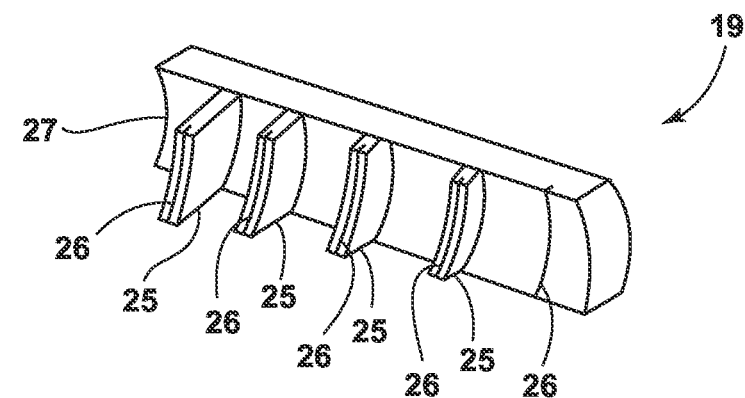
FIG. 5B depicts a perspective view of a needle slide for use with either a cylindrical or conical shaper according to another embodiment.
Figure 5C:
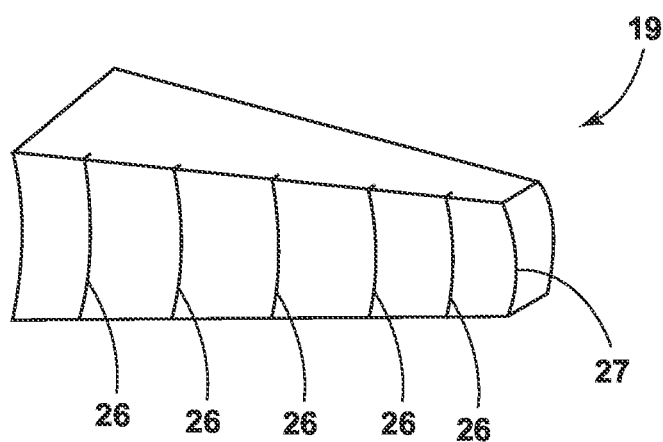
FIG. 5C depicts a perspective view of a needle slide for use with a conical shaper according to yet another embodiment.

FIGS. 5A-5C show embodiments of the needle slide 19. Generally, the needle slide 19 can comprise any suitable structure into which an end of a needle can be inserted and which can slide relative to a needle to be bent as the leverage arm 15 moves. While not shown in FIG. 5A-5C, it is understood that the needle slide 19 can be formed with or otherwise coupled to the leverage arm 15. In one embodiment, the needle slide 19 can comprise an opening or slot in one end of the leverage arm 15 through which the end of a needle is insertable.

As depicted in FIG. 5A, the needle slide 19 may have a substantially uniform shaper engaging surface 27 for contacting the curved outer surface 28 of a cylindrical shaper 12. The shaper engaging surface 27 may accordingly having a curvature that matches or substantially matches that of the curved outer surface 28. The needle slide 19 may have a plurality of needle channels 26 configured to receive and retain a needle to be bent. The needle channels 26 may align with the plurality of grooves 13 in the shaper 12. In all embodiments, the needle channels 26 may be sized to accommodate a variety of needle gauges.

In FIG. 5B, a needle slide 19 which can be used with the embodiments of FIGS. 1-4 is shown. The needle slide 19 may have a plurality of slide ridges 25 extending from the shaper engaging surface 27 of the needle slide 19. Each slide ridge 25 may be configured to align with one of the plurality of grooves 13 in the shaper 12. The slide ridges 25 can each have a needle channel 26 to receive and support a needle to be bent. In one embodiment, each slide ridge 25 may extend a different distance from the shaper engaging surface 27 such that a needle placed in the needle channel 26 will be held at the same distance from the groove 13 as the leverage arm 15 is actuated regardless of the diameter G of the groove 13. As depicted, the needle channel 26 corresponding to the groove 13 with the largest desired needle bend radius is placed in the shaper engaging surface 27 rather than in a slide ridge 25. In an alternative embodiment, the groove 13 with the largest desired needle bend radius may have a corresponding slide ridge 25 in which the needle channel is disposed. In one embodiment, both the lock plate 14 and the needle slide 19 can have ridges 23, 25. In an alternative embodiment, only one of the lock plate 14 and the needle slide 19 may have ridges 23, 25.

In FIG. 5C, a needle slide 19 according to a third embodiment is shown. The needle slide 19 as depicted may be particularly suitable for use with the needle bender 10 in FIG. 4. The needle slide 19 may have a shaper engaging surface 27 that is slanted toward the curved outer surface of the shaper 12 such that shaper engaging surface 27 is a consistent distance from the curved outer surface 28 of the shaper 12. The needle slide 19 may have a plurality of needle channels 26 disposed in the shaper engaging surface 27 for receiving and supporting a portion of a needle to be bent.

Figure 6A:
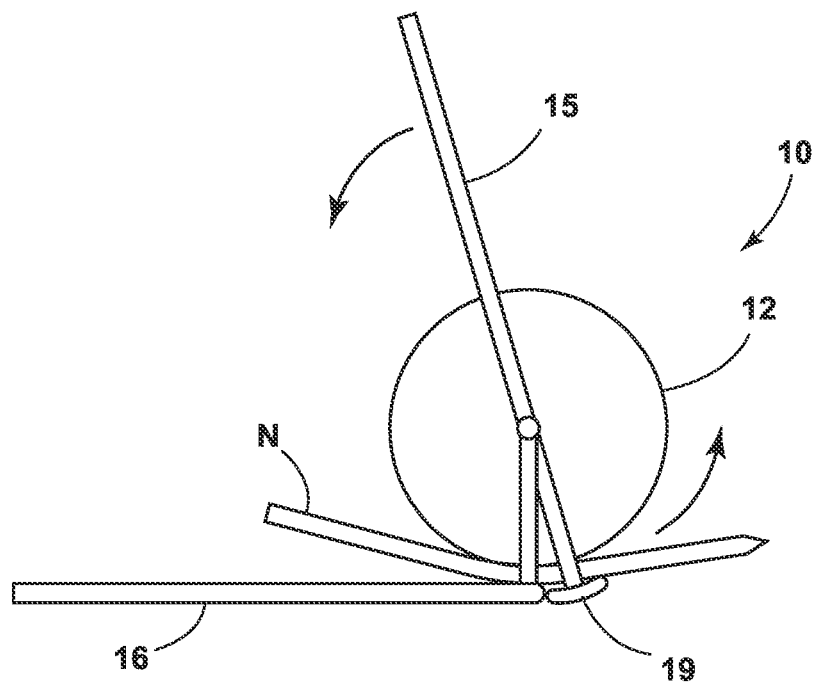
FIGS. 6A-6B depict a method of using the needle bender of FIG. 1 to bend a needle, with FIG. 6A showing a needle loaded into place and FIG. 6B showing the needle being bent.
Figure 6B:
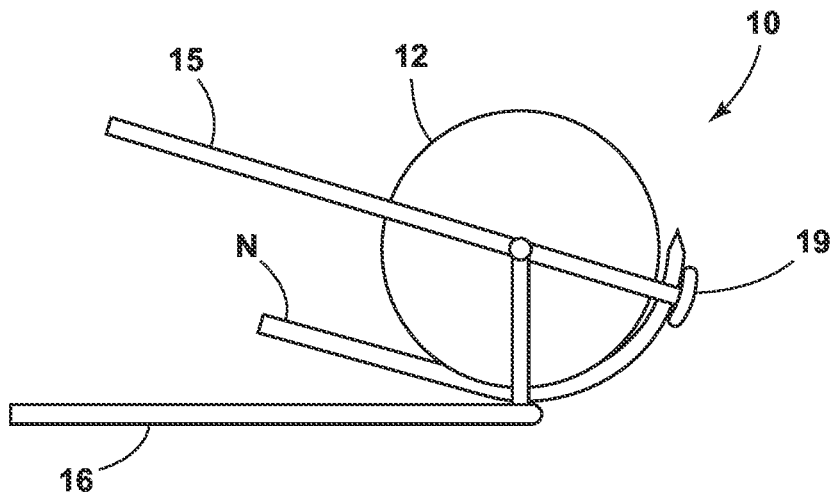

FIGS. 6A-6B depict a method of using a needle bender 10 according to one embodiment to bend a needle N. The method is described for the needle bender 10 of FIGS. 1-2, although it is generally applicable to any embodiment disclosed herein. The leverage arm 15 can be rotated to a first position as shown in FIG. 6A such that the needle slide 19 is substantially in line with the base arm 16. Alternatively, the first position may correspond to the needle slide 19 being substantially in line with the needle gap 22. A needle N may be inserted along the base arm 16 through the needle gap 22 such that a portion of the needle N to be bent extends through and/or along the needle slide 19, and such that the portion of the needle N to be bent is supported by the needle slide 19. In some embodiments, the needle N may be inserted into one of the plurality of grooves 13 in the shaper 12 corresponding to the desired needle bend radius. In an alternative embodiment, the needle N may be inserted along any other location of the shaper 12 corresponding to a desired needle bend radius. The radius of curvature of the bend can depend upon to which groove 13 along the shaper 12 the needle N is anchored. In one embodiment, a portion of the needle N desired to be bent protrudes beyond the shaper 12. The arrows in FIG. 6A indicate the direction of rotation of the leverage arm 15.

The leverage arm 15 can be actuated toward the base arm 16 to a second position, one non-limiting example to which is shown in FIG. 6B, thereby moving the needle slide 19 along the curved outer surface 28 of the shaper 12. As the needle slide 19 moves along the curved outer surface 28 of the shaper 12, the needle slide 19 may apply force to the portion of the needle N to be bent extending through the needle slide 19 such that the needle N is bent around the shaper 12 and the needle N conforms to the desired needle bend radius. In an alternative embodiment, the leverage arm 15 can be actuated a smaller distance to bend a smaller section of the portion of the needle N that extends through the needle slide 19. In an alternative embodiment in which the leverage arm 15 and the shaper 12 rotate as one piece, the rotational force may be sufficient to bend the needle N around the shaper 12. The needle N may then be removed from the needle bender 10 in any suitable manner. For example, the user may grab the blunt end of the needle N and pull it back along the base arm 16 until the needle N is released from the needle bender 10. This may be done with or without actuating the leverage arm 15 back to the first position.

In one embodiment, the needle bender 10 may be placed on a horizontal surface (such as an operating table) while the method is performed. In another embodiment, the needle bender 10 may be permanently secured to a stand or other stationary member. In yet another embodiment, the needle bender 10 may be operated while the user holds the base arm 16.

The needle bender 10 can be operated without the user having to touch the needle point. Therefore, the needle bender 10 may reduce the risk of needle sticks and thus assist the surgical staff in maintaining sterility during surgery. Additionally, the ability to reliably adjust radius of curvature of a needle during surgery by using the needle bender 10 has distinct advantages. It can allow more controlled passing of the needle across tissue, which may result in less tissue disruption, surgical risk, needle breakage, and less risk of collateral tissue damage. The needle bender 10 can be used after the needle N has passed through tissue in a controlled, non-contact fashion to minimize contamination and infection risk. The needle bender 10 can be used to perform controlled bends at any point along the needle N as needed and may be used repeatedly in the surgical field.

In an embodiment where the needle bender 10 includes the lock plate 14, such as the embodiments of FIG. 3 and FIG. 4, the process of bending the needle N may start with the lock plate 14 in a lowered position. The needle N may be inserted along the base arm 16 adjacent the lock plate 14 such that a portion of the needle N to be bent engages and/or extends past the needle slide 19. Alternatively, the needle N may not extend past the needle slide 19. The needle N can be inserted along the base 11 such that the needle N aligns with one of the plurality of grooves 13 in the shaper 12 or aligns with any other portion on the shaper 12 corresponding to a desired needle bend radius. In an alternate embodiment, the needle N can be inserted along the base 11 such that the needle N aligns with any other portion on the shaper 12 corresponding to a desired needle bend radius. The lock plate 14 may then be actuated toward the shaper 12 through turning the at least one set screw 17 such that the needle N is further secured in the selected groove 13. After the needle N is securely anchored, the leverage arm 15 may then be rotated about the axis X by pressing down on the handle 20 until the desired bend is obtained. Pressing down on the handle 20 applies an input force on the leverage arm 15 toward the base arm 16. The lock plate 14 may be actuated away from the shaper 12 by turning the at least one set screw 17 in the opposite direction such that the needle N is released from the shaper 12. The needle N may then be removed from the needle bender 10. If the desired needle bend radius was not achieved, the process may be repeated until the needle N has the desired needle bend radius. The needle N can be bent any number of times to conform to different desired needle bend radii.

In one embodiment, a portion of a needle N may be held within the needle slide 19, such that when the handle 20 is pressed toward the base arm 16 to apply input force to the leverage arm 15, the needle slide 19 applies output force to the needle N to form a bend, while sliding along the length of the needle N.

The above description is that of a current embodiment of the invention. Various changes and alterations can be made without departing from the spirit and broader aspects of the invention.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The embodiments of the invention in which an exclusive property or privilege is claimed are defined as follows:

1. A surgical needle bender comprising:
   a base comprising:
      a base arm; and
      a support member coupled to the base arm;
   a shaper coupled to the base through the support member, the shaper having an axis and a curved outer surface;
   a needle gap between the shaper and the base, the needle gap defining an opening having a height of a first distance, the opening being configured to receive a surgical needle to be bent between the shaper and the base;
   the shaper having a plurality of circumferential grooves in the curved outer surface, each of the grooves having a groove base, each of the grooves having a groove radius that is the radial distance between the shaper axis and the groove base, each of the grooves corresponding to a different desired needle bend radius, whereby the shaper provides a plurality of different radii of curvature bends;
   a leverage arm pivotally coupled to the support member for movement about an axis; and
   a needle slide disposed on one end of the leverage arm adjacent to and spaced from the curved outer surface of the shaper by a second distance, the needle slide having at least one needle channel therein to receive and support at least a portion of a needle to be bent,
   wherein the leverage arm is actuatable from a first position wherein the needle slide is substantially aligned with the needle gap toward the base arm to a second position wherein the needle slide is upwardly displaced along the curved outer surface.

2. The surgical needle bender of claim 1, comprising:
   a lock plate coupled to the base arm; and
   at least one set screw coupled to the lock plate, the at least one set screw being actuatable to secure a needle to be bent between the lock plate and the shaper.

3. The surgical needle bender of claim 2, wherein the lock plate has an upper needle engaging surface facing the curved outer surface of the shaper.

4. The surgical needle bender of claim 3,
   wherein the shaper is cylindrical, and
   wherein a plurality of ridges corresponding to the grooves extend from the upper needle engaging surface, the plurality of ridges extending different distances from the upper needle engaging surface, each of the ridges aligned with one of the grooves in the shaper.

5. The surgical needle bender of claim 1, wherein the shaper is cylindrical.

6. The surgical needle bender of claim 1, wherein the shaper is conical.

7. The surgical needle bender of claim 1, wherein the leverage arm rotates relative to the shaper, enabling the needle slide to remain in contact with the needle as the needle lengthens during bending.

8. The surgical needle bender of claim 1,
   wherein the shaper is pivotally coupled to the support member for movement about the axis, and
   wherein the leverage arm and the shaper rotate as one unit relative to the base arm.

9. The surgical needle bender of claim 1, wherein the leverage arm and the base arm are the same length.

10. The surgical needle bender of claim 1, wherein the base arm is stationary.

11. The surgical needle bender of claim 1, comprising:
    a handle coupled to the leverage arm and disposed on an end of the leverage arm opposite the needle slide.

12. The surgical needle bender of claim 1, wherein the second distance is greater than or equal to the first distance.

13. A needle bender comprising:
    a base comprising:
       a base arm; and
       a support member coupled to the base arm;
    a shaper coupled to the base through the support member, the shaper having a curved outer surface, wherein the shaper is conical;
    a needle gap between the shaper and the base, the needle gap defining an opening having a height of a first distance, the opening being configured to receive a needle to be bent between the shaper and the base;
    the shaper having a plurality of grooves in the curved outer surface, each of the plurality of grooves corresponding to a desired needle bend radius;
    a leverage arm pivotally coupled to the support member for movement about an axis;
    a needle slide disposed on one end of the leverage arm adjacent to and spaced from the curved outer surface of the shaper by a second distance, the needle slide having at least one needle channel therein to receive and support at least a portion of a needle to be bent,
    a lock plate coupled to the base arm, the lock plate having an upper needle engaging surface facing the curved outer surface of the shaper, wherein the upper needle engaging surface is angled with respect to the base; and
    at least one set screw coupled to the lock plate, the at least one set screw being actuatable to secure a needle to be bent between the lock plate and the shaper,
    wherein the leverage arm is actuatable from a first position wherein the needle slide is substantially aligned with the needle gap toward the base arm to a second position wherein the needle slide is upwardly displaced along the curved outer surface.

14. A needle bender comprising:
    a base comprising:
       a base arm; and
       at least one support member coupled to the base arm;
    a lock plate movably coupled to the base arm, the lock plate comprising:
       an upper needle engaging surface, the upper needle engaging surface being angled with respect to the base; and
       a base arm engaging surface, the base arm engaging surface defining at least one opening to movably couple at least one set screw to the lock plate;
    a conical shaper pivotally coupled to the support member for movement about an axis, the conical shaper having a curved outer surface;
    a needle gap between the conical shaper and the lock plate, the needle gap defining an opening having a variable height based on a position of the lock plate;
    the conical shaper having a plurality of grooves in the curved outer surface, each of the plurality of grooves corresponding to a desired needle bend radius;
    a leverage arm coupled to the support member for movement about the axis, the leverage arm coupled to the conical shaper such that the leverage arm and the conical shaper rotate as one unit about the axis; and a needle slide disposed on one end of the leverage arm adjacent to and spaced from the curved outer surface of the conical shaper by a fixed distance, the needle slide having at least one needle channel therein to receive and support at least a portion of a needle to be bent, wherein the at least one set screw is actuatable to move the lock plate vertically with respect to the base arm toward the curved outer surface of the conical shaper, wherein the leverage arm is actuatable from a first position toward the base arm to a second position, wherein in the first position, the needle slide is substantially aligned with the needle gap, and wherein in the second position, the needle slide is upwardly displaced along the curved outer surface.

15. The needle bender of claim 14, wherein the leverage arm is actuatable from the second position to the first position.

16. The needle bender of claim 14, wherein the plurality of grooves are circumferential.

17. The needle bender of claim 14, wherein the leverage arm comprises a handle, the handle being disposed on an end of the leverage arm opposite the needle slide.

18. The needle bender of claim 14, wherein the fixed distance is greater than or equal to the variable height when the lock plate is actuated to its maximum distance from the base arm.

* * * * *